(12) United States Patent
Tu et al.

(10) Patent No.: US 7,378,569 B2
(45) Date of Patent: May 27, 2008

(54) TRANSGENIC PIGS CARRYING BOTH HHO-1 AND HDAF TRANSGENES FOR XENOTRANSPLANTATION

(75) Inventors: Ching-Fu Tu, Miaoli Hsien (TW); Chi-Kai Yang, Miaoli Hsien (TW); Ming-Shing Liu, Miaoli Hsien (TW); Lin-Lin Ho, Miaoli Hsien (TW); Kuei-Feng Huang, Miaoli Hsien (TW); Chun-Jean Lee, Miaoli Hsien (TW); Hao-Chih Tai, Miaoli Hsien (TW)

(73) Assignee: Animal Technology Institute Taiwan (TW)

( * ) Notice: Subject to any disclaimer, the term of this patent is extended or adjusted under 35 U.S.C. 154(b) by 164 days.

(21) Appl. No.: 10/857,613

(22) Filed: Jun. 1, 2004

(65) Prior Publication Data

US 2005/0268347 A1 Dec. 1, 2005

(51) Int. Cl.
  *A01K 67/27* (2006.01)
  *A01K 67/033* (2006.01)
  *C12N 5/00* (2006.01)
(52) U.S. Cl. ............... 800/17; 800/14; 424/93.2
(58) Field of Classification Search .............. 800/17, 800/14; 424/93.2
  See application file for complete search history.

(56) References Cited

OTHER PUBLICATIONS

Cozzi et al., The generation of transgenic pigs as potential organ donors for human, 1995, Nature Medicine, 1:964-966.*
Zhang et al., Animal models in xenotransplantation. Exp. Opin. Invest. Drugs, 2000, 9:2051-2068.*
Logan et al., Potential use of genetically modified pigs as organ donors for transplantation into humans. Clin Exp Pharmacol Physiol. Dec. 1999;26(12):1020-5. Review.*
Murphy, L.J and Silha, J.V., Unexpected and unexplained phenotypes in transgenic models. Growth Hormone and IGF Research, 10:233-235, 2000.*
Sigmund. Viewpoint: are studies in genetically altered mice out of control?Arterioscler Thromb Vasc Biol. Jun. 2000;20(6):1425-9. Review.*
Hammer et al.,Spontaneous inflammatory disease in transgenic rats expressing HLA-B27 and human beta 2m: an animal model of HLA-B27-associated human disorders. Cell. Nov. 30, 1990;63(5):1099-112.*
Kappel, Regulating gene expression in transgenic animals. Current Biology, 3:548-553, 1992.*
Williams and Wagner, Transgenic animals in integrative biology: approaches and interpretation. J. Appl. Physiol., 88:1119-1126, 2000.*
Niemann, Transgenic farm animals get off the ground. 1997, Transg. Res. 7:73-75.*
Nebert et al., How knockout mouse lines will be used to study the role of drug-metabolizing enzymes and their receptors during reproduction and development, in environmental toxicity, cancer, and oxidative stress. Biochem Pharmacol. Feb. 7, 1997;53(3):249-54. Review.*
McCurry et al., Human complement regulatory proteins swine-to-primate cardiac xenografts from humoral injury.Nat Med. May 1995;1(5):423-7.*
Yet SF aet al., Cardiac-specific expression of heme oxygenase-1 protects against ischemia and reperfusion injury in transgenic mice. Circ Res. Jul. 20, 2001;89(2):168-173.*
Cooper, "Is Xenotransplantation a realistic clinical option?", *Transplant. Proc.*, 1992: 24:2393-2396.
Nowak, "Xenotransplants set to resume", *Science*, 1994: 266:1148-1151.
Cozzi, "Expression of human decay accelerating factor in transgenic pigs", *Transplant. Proc.*, 1994; 26:1402-1403.
McCurry, "Human complement regulatory proteins protect swine-to-primate cardiac xenografts from humoral injury", *Nature Med.*, 1995; 1:423-427.
Fodor, "Expression of a functional human complement inhibitor in a transgenic pig as a model for the prevention of xenogeneica hyperacute organ rejection", *Proc. Natl. Acad. Sci.*, 1994; 91:11153-11157.
Schmoeckel, "Prevention of hyperacute rejection by human decay accelerating factor in xenogeneic perfused working hearts", *Transplantation*, 1996; 62:729-734.
Byrne, "Transgenic pigs expressing human CD59 and decay-accelerating factor produce an intrinsic barrier to complement-mediated damage", *Transplantation*, 1997; 63:149-155.
Kroshus, "Expression of human CD59 in transgenic pig organs enhance organ survival in an ex vivo xenogeneic perfusion model", *Transplantation*, 1997; 61: 1513-1521.
Storck, "Morphology of hDAF (CD55) transgenic pig kidneys following ex-vivo hemoperfusion with human blood", *Transplantation*, 1997; 63:304-310.
Pierson, "Expression of human decay accelerating factor may protect pig lung from hyperacute rejection by human blood", *J. Heart and Lung Trans.*, 1997; 16:231-239.
Diamond, "Characterization of transgenic pigs expressing functionally active human CD59 on cardiac endothelium", *Transplantation*, 1996; 61:1241-1249.
Cozzi, "Long-term survival of nonhuman primates receiving life-supporting transgenic porcine kidney xenografts", *Transplant. Proc.*, 2000; 70:15-21.
Vial, "Life supporting function for over one month of a transgenic porcine heart in a baboon", *J. Heart Lung Transplant*, 2000; 19:224-229.

(Continued)

*Primary Examiner*—Anne M. Wehbe
*Assistant Examiner*—Maria Leavitt
(74) *Attorney, Agent, or Firm*—Rothwell, Figg, Ernst & Manbeck P.C.

(57) ABSTRACT

The invention provides a transgenic animal carrying two transgenes, one encoding a human decay accelerating factor (hDAF) and the other encoding a human heme oxygenase-1 (hHO)-1, which are useful for providing cells, tissues or organs therefrom for xenotransplantation.

5 Claims, 13 Drawing Sheets

OTHER PUBLICATIONS

Galili, "The natural anti-gal antibody: evolution and autoimmunity in man", *Immunol. Ser.*; 1991; 55:355-373.

Galili, "Man, apes, and old world monkeys differ from other mammals in the expression of α-galactosyl epitopes on nucleated cells", *J. Biol. Chem.*; 1988; 263:17755-17762.

Larsen, "Isolation of a cDNA encoding a murine UDPgalactose:$\beta $-D-galactosyl-1,4-N-acetyl-D-glucosaminide $\alpha $-1,3-galactosyltransferase: expression cloning by gene transfer", *PNAS*, 1989; 86:8227-8231.

Larsen, R., "Frameshift and nonsense mutations in a human genomic sequence homologous to a murine UPD-Gal:β-D-Gal(1,4)-D-GlcNAc α(1,3)-galactosyltransferase cDNA", *J. Biol. Chem.*, 1990: 265:7055-7061.

Sandrin, M., "Characterization of cDNA clones for porcine α(1,3)galatosyl transferase: The enzyme generating the Galα(1,3)Gal epitope", *Xenotransplantation*, 1994; 1:81-88.

Joziasse, D., "Characterization of an α1-3-Gaactosyltransferase Homologue on human chromosome 12 that is organized as a processed pseudogene", *J. Biol. Chem.*, 1991; 266:6991-6998.

Dai, Y., "Targeted disruption of the α1,3-galactosyltransferase gene in cloned pigs", *Nature Biotech.*, 2002; 20:251-255.

Lai, L., "Production of α-1,3-galactosyltransferase knockout pigs by nuclear transfer cloning", *Science*, 2002; 295:1089-1092.

Phelps, C., "Production of α-1,3-galactosyltransferase-deficient pigs", *Science*, 2002; 299:411-414.

Sharma, A., "Reduction in the level of Gal($\alpha $1,3)Gal in transgenic mice and pigs by the expression of an $\alpha $(1,2)fucosyltransferase", *PNAS*, 1996; 93:7190-7195.

Maines, M., "The heme oxygenase system: A regulator of second messenger gases", *Ann. Rev. Pharmacol. Toxicol.*, 1997; 37:517-554.

Choi, A., "Heme oxygenase-1: function, regulation, and implication of a novel stress-inducible protein in oxidant-induced lung injury", *Am. Journ. Of Resp. Cell and Molecular. Biol.*, 1996; 15:9-19.

Poss, K., "Reduced stress defense in heme oxygenase 1-deficient cells", *Proc. Natl. Acad. Sci. of USA*, 1997; 94:10925-10930.

Poss, K., "Heme oxygenase 1 is required for mammalian iron reutilization", *Proc. Natl. Acad. Sci. of USA*, 1997; 94:10919-10924.

Soares, M., "Expression of heme oxygenase-1 can determine cardiac xenograft survival", *Nature Medicine*, 1998; 4:1073-1077.

Yachie, A., "Oxidative stress causes enhanced endothelial cell injury in human heme oxygenase-1 deficiency", *J. of Clin. Invest.*, 1999; 103:129-135.

Sato, K., Carbon monoxide generated by heme oxygenase-1 suppresses the rejection of mouse-to-rat cardiac transplants, *J. Immun.*, 2001; 166:4185-4194.

Pileggi, A., "Heme oxygenase-1 induction in islet cells result in protection from apoptosis and improved in vivo function after transplantation", *Diabetes*; 2001; 50:1983-1991.

Otterbein, L., "Exogenous administration of heme oxygenase-1 by gene transfer provides protection against hyperoxia-induced lung injury", *J. of Clin. Invest.*, 1999; 103:1047-1054.

Amersi, F., "Upregulation of heme oxygenase-1 protects genetically fat zucker rat livers from ischemia/reperfusion injury", *J. Clin. Invest.*, 1999; 104:1631-1639.

Shiraishi, F., "Heme oxygenase-1 gene ablation or expression modulates cisplatin-induced renal tubular apoptosis", *Am. J. Physiol Renal Physiol.*, 2000; 278:F726-F736.

Minamino, T., "Targeted expression of heme oxygenase-1 prevents the pulmonary inflammatory and vascular responses to hypoxia", *PNAS*, 2001; 98:8798-8803.

Yet, S., "Cardiac-specific expression of heme oxygenase-1 protects against ischemia and reperfusion injury in transgenic mice", *Cir. Res.*, 2001; 89:168-173.

Medof, M., "Cloning and characterization of cDNAs encoding the complete sequence of decay-accelerating factor of human complement", *Proc. Natl. Acad. Sci. USA*, 1987; 84:2007-2011.

Yoshida, T., "Human heme oxygenase cDNA and induction of its mRNA by hemin", *Eur. J. Biochem.*, 1988; 171:457-461.

Tu, C., "Generation of HLA-DP transgenic pigs for the study of xenotransplantation", *Int Surg.*, 1999; 84:176-182.

Tu, C., "The integration and expression in transgenic pigs for hDAF/hDO-1 double genes", *Xenotransplantation*, 2003; 10:503.

Lee, K., "Routine generation of green fluorescent chimeric mice with a high percentage of germline transmission by a novel embryonic stem cell line", *J. Chin. Soc. Anim. Sci.*, 2003; 32;143-154.

Su et al., "Spatiotemporal expression of heme oxygenase-1 detected by in vivo bioluminescence after hepatic ischemia in HO-1/Luc mice.", *Liver Transpl.*, Nov. 2006;12(11):1634-9. (PubMed abstract only).

Desandre et al., "The effectiveness of oral tin mesoporphyrin prophylaxis in reducing bilirubin production after an oral heme load in a transgenic mouse model.", *Biol Neonate*, 2006;89(3):139-46. Epub Oct. 3, 2005 (PubMed abstract only).

Tu et al., "Effects of heme oxygenase-1 transgenic islets on transplantation.", *Transplant Proc.*, Oct. 2005;37(8):3463-7. (PubMed abstract only).

Weinzierl et al., "Endothelin-mediated induction of heme oxygenase-1 in the spinal cord is attenuated in transgenic mice overexpressing superoxide dismutase.", *Brain Res.*, Dec. 24, 2004;1030(1):125-32. (PubMed abstract only).

Araujo et al., "Systemic rather than local heme oxygenase-1 overexpression improves cardiac allograft outcomes in a new transgenic mouse.", *J Immunol.*, Aug. 1, 2003;171(3):1572-80. (PubMed abstract only).

Braudeau et al., "Generation of heme oxygenase-1-transgenic rats.", *Exp Biol Med* (Maywood)., May 2003;228(5):466-71. (PubMed abstract only).

Zampetaki et al., "Effect of heme oxygenase-1 overexpression in two models of lung inflammation.", *Exp Biol Med* (Maywood)., May 2003;228(5):442-6. (PubMed abstract only).

Vulapalli et al., "Cardioselective overexpression of HO-1 prevents I/R-induced cardiac dysfunction and apoptosis.", *Am J Physiol Heart Circ Physiol.*, Aug. 2002;283(2):H688-94. (PubMed abstract only).

Maines, "Heme oxygenase 1 transgenic mice as a model to study neuroprotection.", *Methods Enzymol.*, 2002;353:374-88. (PubMed abstract only).

Zhang et al., "Rapid in vivo functional analysis of transgenes in mice using whole body imaging of luciferase expression.", *Transgenic Res.*, Oct. 2001;10(5):423-34. (PubMed abstract only).

Yet et al., "Cardiac-specific expression of heme oxygenase-1 protects against ischemia and reperfusion injury in transgenic mice.", *Circ Res.*, Jul. 20, 2001;89(2):168-73. (PubMed abstract only).

Minamino et al., "Targeted expression of heme oxygenase-1 prevents the pulmonary inflammatory and vascular responses to hypoxia." *Proc Natl Acad Sci U S A.*, Jul. 17, 2001;98(15):8798-803. Epub Jul. 10, 2001. (PubMed abstract only).

Nath et al., "Oxidative stress and induction of heme oxygenase-1 in the kidney in sickle cell disease.", *Am J Pathol.*, Mar. 2001;158(3):893-903. (PubMed abstract only).

Shiraishi et al., "Heme oxygenase-1 gene ablation or expression modulates cisplatin-induced renal tubular apoptosis.", *Am J Physiol Renal Physiol.*, May 2000;278(5):F726-36. (PubMed abstract only).

Panahian et al., "Overexpression of heme oxygenase-1 is neuroprotective in a model of permanent middle cerebral artery occlusion in transgenic mice.", *J Neurochem.*, Mar. 1999;72(3):1187-203. (PubMed abstract only).

Morgan et al., "Impaired spatial navigation learning in transgenic mice over-expressing heme oxygenase-1.", *Brain Res.*, Oct. 12, 1998;808(1):110-2. (PubMed abstract only).

Maines et al., "Neuronal overexpression of heme oxygenase-1 correlates with an attenuated exploratory behavior and causes an increase in neuronal NADPH diaphorase staining.", *J Neurochem.*, May 1998;70(5):2057-69. (PubMed abstract only).

Pappolla et al., "Evidence of oxidative stress and in vivo neurotoxicity of beta-amyloid in a transgenic mouse model of Alzheimer's disease: a chronic oxidative paradigm for testing antioxidant therapies in vivo.", *Am J Pathol.*, Apr. 1998;152(4):871-7. (PubMed abstract only).

\* cited by examiner

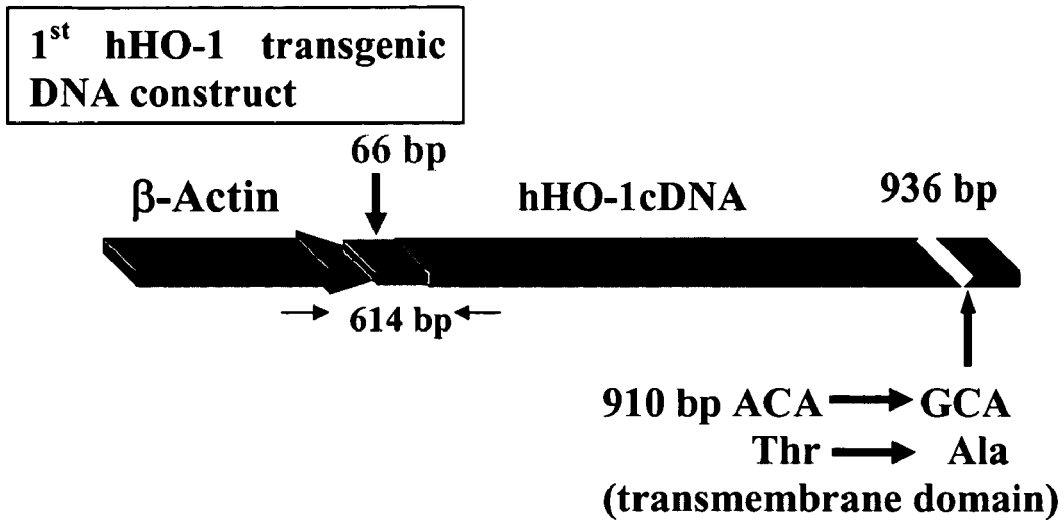
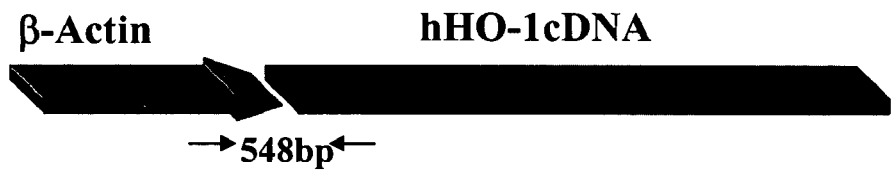
Figure 1

Figure 2

```
taacccggga attcatgacc gtcgcgcggc cgagcgtgcc cgcggcgctg cccctcctcg   60
gggagctgcc ccggctgctg ctgctggtgc tgttgtgcct gccggccgtg tggggtgact  120
gtggccttcc cccagatgta cctaatgccc agccagcttt ggaaggccgt acaagttttc  180
ccgaggatac tgtaataacg tacaaatgtg aagaaagctt tgtgaaaatt cctggcgaga  240
aggactcagt gatctgcctt aagggcagtc aatggtcaga tattgaagag ttctgcaatc  300
gtagctgcga ggtgccaaca aggctaaatt ctgcatccct caaacagcct tatatcactc  360
agaattattt tccagtcggt actgttgtgg aatatgagtg ccgtccaggt tacagaagag  420
aaccttctct atcaccaaaa ctaacttgcc ttcagaattt aaaatggtcc acagcagtcg  480
aattttgtaa aaagaaatca tgccctaatc cgggagaaat acgaaatggt cagattgatg  540
taccaggtgg catattattt ggtgcaacca tctccttctc atgtaacaca gggtacaaat  600
tatttggctc gacttctagt ttttgtctta tttcaggcag ctctgtccag tggagtgacc  660
cgttgccaga gtgcagagaa atttattgtc cagcaccacc acaaattgac aatggaataa  720
ttcaagggga acgtgaccat tatggatata gacagtctgt aacgtatgca tgtaataaag  780
gattcaccat gattggagag cactctattt attgtactgt gaataatgat gaaggagagt  840
ggagtggccc accacctgaa tgcagaggaa aatctctaac ttccaaggtc ccaccaacag  900
ttcagaaacc taccacagta aatgttccaa ctacagaagt ctcaccaact tctcagaaaa  960
ccaccacaaa aaccaccaca ccaaatgctc aagcaacacg gagtacacct gtttccagga 1020
caaccaagca ttttcatgaa acaaccccaa ataaggaag tggaaccact tcaggtacta 1080
cccgtcttct atctgggcac acgtgtttca cgttgacagg tttgcttggg acgctagtaa 1140
ccatggcgtt gctgacttag ccaaagaaga gttaagaaga aaatacacac aagtatacag 1200
actgttccta gtttcttaga cttatctgca tattggataa aataaatgca attgtgctct 1260
tcaaaaaaaa aaaaaaaaaa ctcgagaatt catctagagg gccctat            1307
```

Figure 3

| | | | | | | |
|---|---|---|---|---|---|---|
| tcaacgccga | attccctcg | agcgtcctca | gcgcagccgc | cgcccgcgga | gccagcacga | 60 |
| acgagcccag | caccgaattc | atggagcgtc | cgcaacccga | cagcatgccc | caggatttgt | 120 |
| cagaggccct | gaaggaggcc | accaaggagg | tgcacaccca | ggcagagaat | gctgagttca | 180 |
| tgaggaactt | tcagaagggc | caggtgaccc | gagacggctt | caagctggtg | atggcctccc | 240 |
| tgtaccacat | ctatgtggcc | ctggaggagg | agattgagcg | caacaaggag | agcccagtct | 300 |
| tcgccctgt | ctacttccca | gaagagctgc | accgcaaggc | tgccctggag | caggacctgg | 360 |
| ccttctggta | cgggccccgc | tggcaggagg | tcatcccta | cacaccagcc | atgcagcgct | 420 |
| atgtgaagcg | gctccacgag | gtggggcgca | cagagcccga | gctgctggtg | gcccacgcct | 480 |
| acacccgcta | cctgggtgac | ctgtctgggg | gccaggtgct | caaaaagatt | gcccagaaag | 540 |
| ccctggacct | gcccagctct | ggcgagggcc | tggccttctt | caccttcccc | aacattgcca | 600 |
| gtgccaccaa | gttcaagcag | ctctaccgct | cccgcatgaa | ctccctggag | atgactcccg | 660 |
| cagtcaggca | gagggtgata | gaagaggcca | agactgcgtt | cctgctcaac | atccagctct | 720 |
| ttgaggagtt | gcaggagctg | ctgacccatg | acaccaagga | ccagagcccc | tcacgggcac | 780 |
| cagggcttcg | ccagcgggcc | agcaacaaag | tgcaagattc | tgccccgtg | gagactccca | 840 |
| gagggaagcc | cccactcaac | acccgctccc | aggctccgct | tctccgatgg | gtccttacac | 900 |
| tcagctttct | ggtggcgaca | gttgctgtag | ggctttatgc | catgtgaatg | caggcatgct | 960 |
| ggctcccagg | gccatgaact | ttgtccggtg | gaaggccttc | tttctagaga | gggaattctc | 1020 |
| ttggctggct | ccttta | 1036 | | | | |

Figure 4

# TRANSGENIC PIGS CARRYING BOTH HHO-1 AND HDAF TRANSGENES FOR XENOTRANSPLANTATION

FIELD OF THE INVENTION

The invention relates to a transgenic animal carrying two transgenes, one encoding a human decay accelerating factor (hDAF) and the other encoding a human heme oxygenase-1 (hHO)-1, which are useful for providing cells, tissues, and organs for xenotransplantation.

BACKGROUND OF THE INVENTION

Because of the insufficient supply of human organs, various xenogeneic sources have been studied for transplantation (Cooper D K. Transplant Proc. 1992; 24: 2393-2396). In this regard, a pig model for transplantation has been developed. However, the use of pigs as an organ source is limited because transplantation of pigs' organs to human bodies results in various immunological rejections to the grafted organs in the human bodies, including hyperacute rejection, delay xenograft rejection (DXR) including acute vascular rejection (also called delay vascular rejection) and acute cellular rejection, and chronic rejection (Nowak R., Science 1994; 266: 1148-1151). It was found that human decay accelerating factor (hDAF, also named CD55; Cozzi et al., Transplant Proc. 1994; 26: 1402-1403 and McCurry et. al., Nat. Med. 1995; 1: 423-427), membrane cofactor protein (MCP; McCurry et. al. supra), and CD59 (McCurry et. al. supra; and Fodor et al., Proc. Natl. Acad. Sci. USA 1994; 91: 11153-11157) can down-regulate the pathway of complement activation, and thus conquers hyperacute rejection to the organs from transgenic pigs. In ex-vivo perfusion studies, hyperacute rejection was prevented in the heart (Schmoeckel et al. Transplantation 1996; 62: 729-734; and Byrne et al., Transplantation 1997; 63: 149-155), kidney (Byrne et al. Supra, Kroshus et al., Transplantation 1996; 61: 1513-1521, Storck et al., Transplantation 1997; 63: 304-310) and lung (Kroshus et al. Supra, Storck et al. Supra, and Pierson R et al., J. Heart Lung Transplant 1997; 16: 231-239) of the transgenic pig introduced with a gene encoding hDAF or CD59. It was also demonstrated that expression of a functional human CD59 on cardiac endothelium of a transgenic pig inhibits the assembling of membrane attack complex, and reduces damages on the heart tissue of a baboon, to which the heart of the transgenic pig was transplanted (Diamond et al., Transplantation 1996; 61: 1241-1249). In addition, the Imutran Limited has provided data showing that transplantation of the kidney and heart from a hDAF transgenic pig to a non-human primate recipient allows the recipient to maintain a life period of over 78 days and one month, respectively (Cozzi et al., Transplantation 2000; 70: 15-21, and Vial et al., J. Heart Lung Transplant. 2000; 19: 224-229.)

In addition, problems regarding natural antibodies generated in human recipients against the epitope of gal-alpha1, 3-gal (i.e., alpha-Gal) carried by endothelial cells of donors' organs remain to be solved. Alpha-Gal is expressed in various tissues, especially the endothelial cells of capillaries, arterioles and arteries, and also in the parencyma of liver, proximal convoluted tubules, glomerulii and collecting ducts of kidney, alveoli of lung, and pancreas ducts (Sandrin M. S. and I. F. C. McKenzie. 1999. Modulation of α-Gal epitope expression on porcine cells. In: α-Gal and anti-Gal: α-1,3-Galactosyltransferase, α-Gal epitope, and the nature anti-Gal antibody. pp. 311-337). The synthesis of the epitope of alpha-Gal depends on the activity of the enzyme, alpha1, 3-galactosyltransferase (i.e., a1, 3-GT) (Galili, U. Immun. Series, 1991; 55:355-337). This enzyme is active in New World monkeys (Galili, U. et al., J. Biol. Chem. 1988; 263:17755-17762), in most species including microbias (Larsen, R. D. et al., Proc. Natl. Acad. Sci. USA. 1989; 86:8227-8231), but not in ape, Old World monkeys and human (Galili, U. supra), wherein in human the α1, 3-GT gene is present as a processed pseudogene, which is non-functional due to frame shift mutations (Larsen, R. D. et al., J. Biol. Chem. 1990; 265:7055-7061). The gene encoding α1, 3-GT has been analyzed in mice (Sandrin, M. S. et al., Xenotransplantation 1994; 1:81-88.) and pigs (Joziasse, D. H. et al., J. Biol. Chem. 266: 6991-6998). It has been suggested that organs of genetically modified pigs in which the α1, 3-GT gene is knocked out might be suitable for xenograft. Recently, α1, 3-GT genetic knockout heterozygote (Dai Y et al., Nature Biotech. 2002; 20: 251-255, and Lai L et al., Science 2002; 295: 1089-1092) and homozygote (Phelps C J et al., Science 2002; 299:411-414) pigs have been cloned. However, the applicability of the α1, 3-GT genetic knockout pigs in xenograft remains to be elucidated. Alternatively, a strategy for competitively inhibiting the alpha-Gal expression in pigs' organs by transgenesis of alpha 1, 2-fucosyltransferase was reported but failed since the alpha-Gal was still expressed with a high density in the pigs' tissues (Sharma A et al., Proc. Natl. Acad. Sci. USA 1996; 93: 7190-7195).

Therefore, there is a need to develop a transgenic animal for providing a graft to be transplanted to a human subject in need thereof, wherein one or more immunological rejections to the graft in the human subject are reduced.

Heme oxygenases (HOs), rate-limiting enzymes in heme catabolism, also named HSP32, belong to members of heat shock proteins, wherein the heme ring is cleaved into ferrous iron, carbon monoxide (CO) and biliverdin that is then converted to bilirubin by biliverdin reductase. Three isoforms of HOs, including HO-1, HO-2 and HO-3, have been cloned. The expression of HO-1 is highly inducible, whereas HO-2 and HO-3 are constitutively expressed (Maines M D et al., Annual Review of Pharmacology & Toxicology 1997; 37:517-554, and Choi A M et al., American Journal of Respiratory Cell & Molecular Biology 1996; 15:9-19). An analysis of HO-1−/− mice suggests that the gene encoding HO-1 regulates iron homeostasis and acts as a cytoprotective gene having potent antioxidant, anti-inflammatory and anti-apoptotic effects (Poss K D et al., Proceedings of the National Academy of Sciences of the United States of America 1997; 94:10925-10930, Poss K D et al., Proceedings of the National Academy of Sciences of the United States of America 1997; 94:10919-10924, and Soares M P et al., Nature Medicine 1998; 4:1073-1077). Similar findings were recently described in a case report of HO-1 deficiency in humans (Yachie A et al., Journal of Clinical Investigation 1999; 103:129-135). The molecular mechanisms responsible for the cytoprotective effects of HO-1, including anti-inflammation, anti-oxidation and anti-apoptosis, are mediated by its' reaction products.

HO-1 expression can be modulated in vitro and in vivo by protoporphyrins with different metals. Cobalt protoporphyrins (CoPP) and iron protoporphyrins (FePP) can up-regulate the expression of HO-1. In contrast, tin protoporphyrins (SnPP) and zinc protoporphyrins (ZnPP) inhibit the activity of HO-1 at the protein level. Recently, it has been proved that the expression of HO-1 suppresses the rejection of mouse-to-rat cardiac transplants (Sato K et al., J. Immunol. 2001; 166:4185-4194), protects islet cells from apoptosis, and improves the in vivo function of islet cells after transplantation (Pileggi A et al., Diabetes 2001; 50: 1983-1991). It has also been proved that administration of HO-1 by gene transfer provides protection against hyperoxia-induced lung injury (Otterbein L E et al., J Clin Invest 1999; 103: 1047-1054), upregulation of HO-1 protects genetically fat Zucker rat livers from ischemia/reperfusion injury (Amersi F et al., J Clin Invest 1999; 104: 1631-1639), and ablation or expression of HO-1 gene modulates cisplatin-induced renal tubular apoptosis (Shiraishi F et al., Am J Physiol Renal Physiol 2000; 278:F726-F736). In transgenic animal models, it was shown that over-expression of HO-1 prevents the pulmonary inflammatory and vascular responses to hypoxia (Minamino T et al., Proc. Natl. Acad. Sci. USA 2001; 98:8798-8803) and protects heart against ischemia and reperfusion injury (Yet S F, et al., Cir Res 2001; 89:168-173).

So far, no transgenic pigs carrying both hDAF and hHO-1 transgenes have been developed for xenotransplantation, and no related teachings and motivation have been provided.

SUMMARY OF THE INVENTION

In one aspect, the invention relates to a transgenic animal comprising two transgenes in its genome, one being an hDAF transgene comprising a nucleotide sequence encoding an hDAF protein and the other being an hHO-1 transgene comprising a nucleotide sequence encoding an hHO-1 protein. In one embodiment, the transgenic animal of the invention is a pig.

In another aspect, the invention provides cells, tissues and organs isolated from the transgenic pig for xenotransplantation.

BRIEF DESCRIPTION OF THE DRAWING

FIG. 1 is a diagram of the first hHO-1 transgenic DNA construct (the upper part) and the second hHO-1 transgenic DNA construct (the lower part) prepared in Example A.3.

FIG. 2 is a diagram of the first hDAF transgenic DNA construct (the upper part) and the second hDAF transgenic DNA construct (the lower part) prepared in Example A.3.

FIG. 3 illustrates the nucleotide sequence (SEQ ID NO: 1) encoding the hDAF protein in one embodiment of the invention. The underlined nucleotide sequences at 5- and 3-ends corresponds to the primers, i.e., CD55-5' (SEQ ID NO: 7) and CD55-3' (SEQ ID NO: 8), used in Example A.2, respectively.

FIG. 4 illustrates the nucleotide sequence (SEQ ID NO: 2) encoding the hHO-1 protein in one embodiment of the invention. The nucleotide sequences recited in the open boxes at 5- and 3-ends corresponds to the primers, i.e., hHO-1cDNA-5' (SEQ ID NO: 3) and hHO-1cDNA-3' (SEQ ID NO: 4), used in Example A.1, respectively. The region in the underlined nucleotide sequences at 5- and 3-ends corresponds to the primers, HO-1Tgc-5' (SEQ ID NO: 5) and HO-1Tgc-3' (SEQ ID NO: 6), used in Example A. 1, respectively.

Panels A to G represent the results of the transgenic pig lines Y25-11A (10X), Y25-13A (10X), Y99-02 (which is an F1 offspring of Y62-11A; 20X), Y280-11a (10X), Y25-12a (20X), Y25-12a (10X), Y15-11a (20X); and Panel H represents the results of a normal non-transgenic pig (10X).

Figure 12:
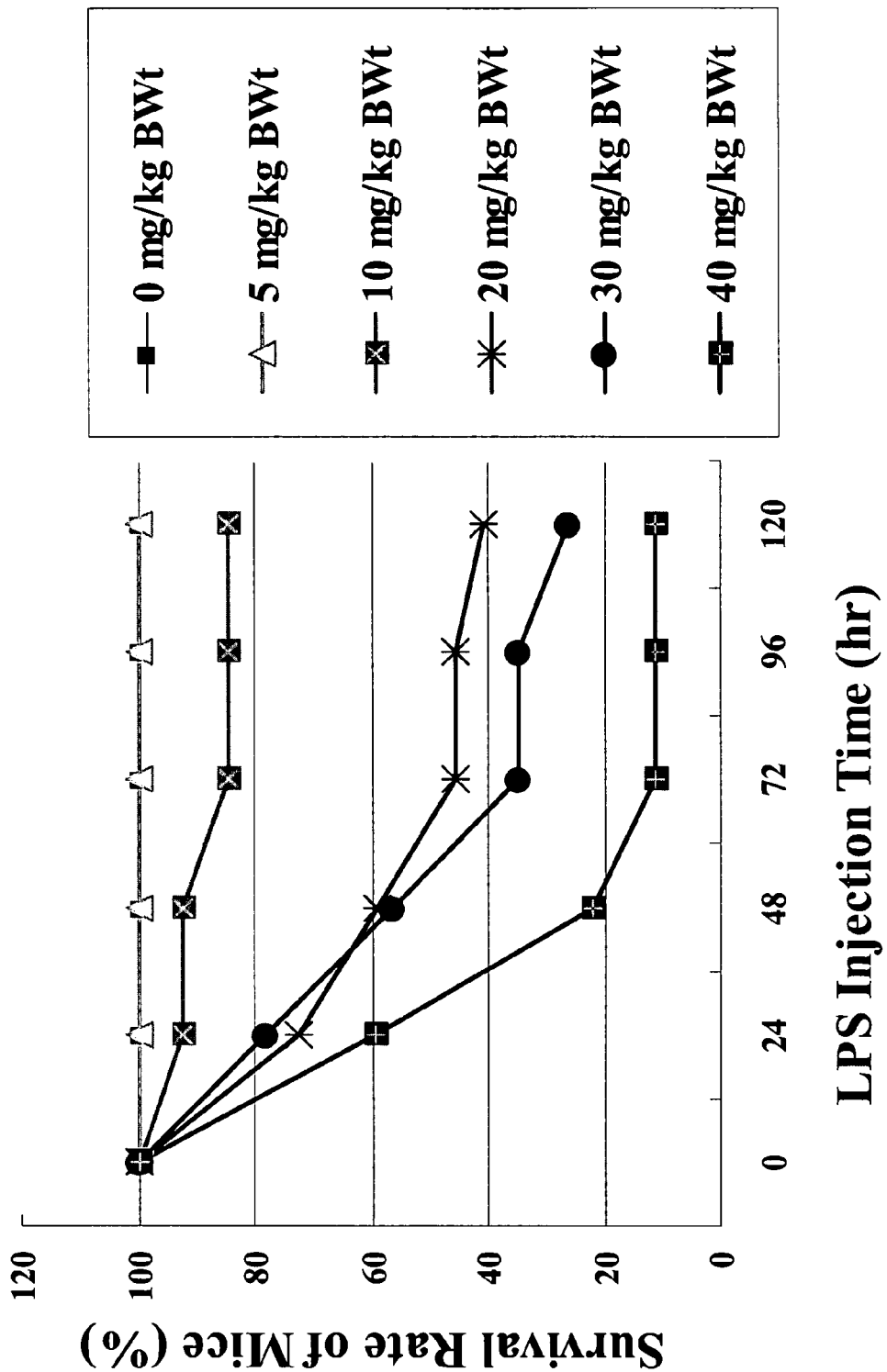

FIG. 12 illustrates the dose-response results of a preliminary test of the LPS challenge assay conducted in normal mice.

Figure 13:
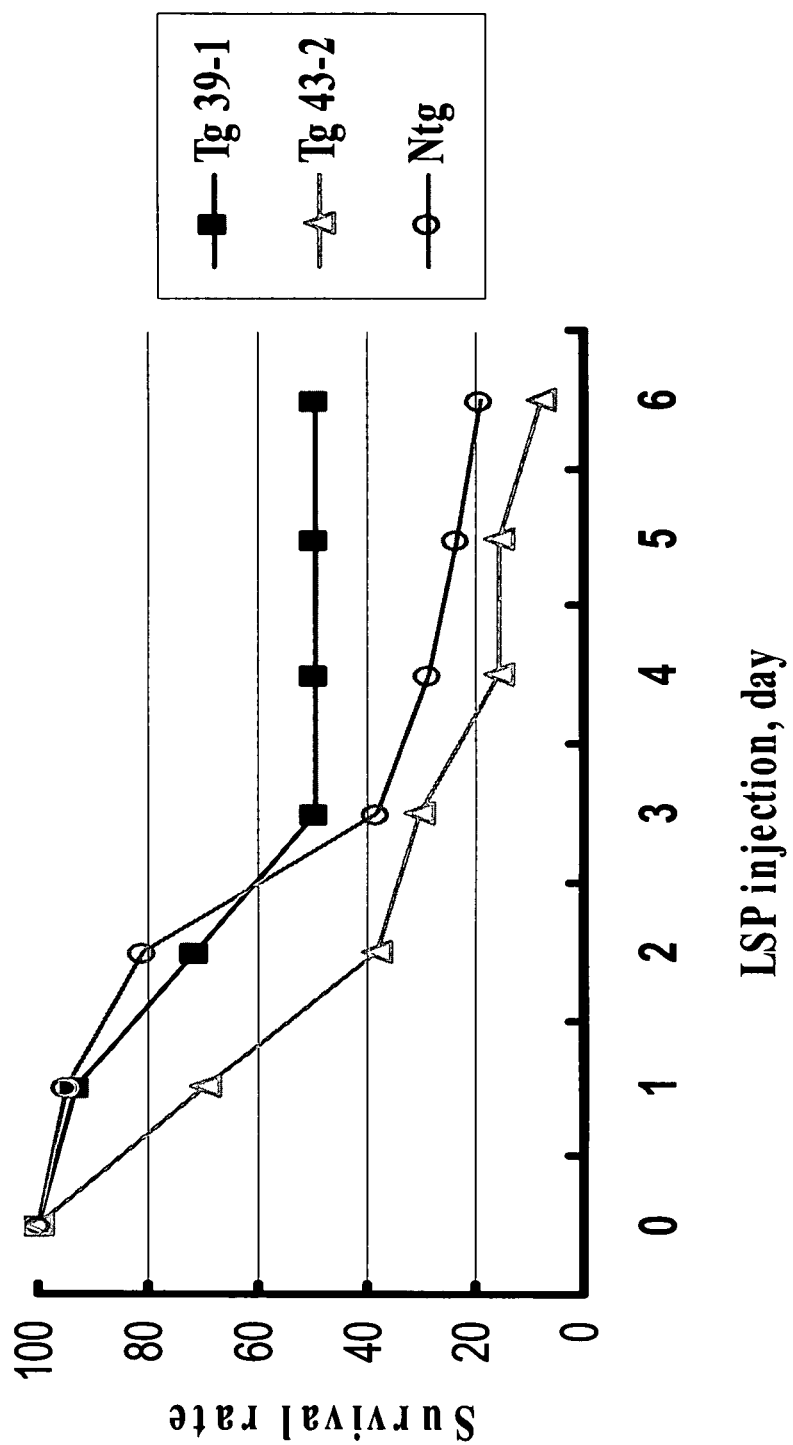

FIG. 13 illustrates the results of the LPS challenge assay conducted in the transgenic mice lines 39-1 (Tg 39-1) and 43-2 (Tg 43-2) generated according to the invention and normal non-transgenic mice (Ntg).

DETAILED DESCRIPTION OF THE INVENTION

I. Definition

The term "transgene" used herein refers to a nucleic acid molecule encoding a foreign protein, which is partly or entirely heterologous to a transgenic animal wherein the transgene is to be placed in its genome. According to the invention, two transgenes are used. One is an hDAF transgene, which comprises a nucleotide sequence encoding an hDAF protein, and the other one is an hHO-1 transgene, which comprises a nucleotide sequence encoding an hHO-1 protein.

The term "transgenic animal" use herein refers to an animal comprising a transgene in its genome. In one embodiment, the transgenic animal of the invention is a pig. Preferably, at least some cells, tissues or organs of the transgenic animal express the hDAF and hHO-1 proteins encoded by the transgenes.

The term "operatically linked" used herein refer to the linkage of nucleic acid elements in a manner such that a selected nucleotide sequence can express the product, e.g., a functional protein, encoded by the selected nucleotide sequence.

The terms "promoter" used herein refer to a nucleic acid element that is preferably located at the 5' end (i.e., upstream) of a nucleotide sequence and provides a site for initiation of transcription of the nucleotide sequence into mRNA.

II. Transgenic Animal of the Invention

In one aspect, the invention relates to a transgenic animal comprising two transgenes in its genome, one being an hDAF transgene comprising a nucleotide sequence encoding an hDAF protein and the other being an hHO-1 transgene comprising a nucleotide sequence encoding an hHO-1 protein. In one embodiment of the invention, the transgenic animal is a pig.

The nucleotide sequences encoding an hDAF protein and an hHO-1 protein have been well characterized and described in the prior art references, e.g., Medof M E et al., have described an hDAF cDNA sequence, i.e., NM 000574 (SEQ ID NO: 1; FIG. 3), in Proceedings of the National Academy of Sciences of the United States of America 1987; 84:2007-2011, and Yoshida T et al., have described an hHO-1 cDNA sequence, i.e., NM 002133 (SEQ ID NO: 2; FIG. 4), in Yoshida T et al., Eur. J. Biochem. 1988; 171 (3): 457-461. Persons skilled in the art can readily obtain the nucleotide sequences and select appropriate ones from the prior art references for the preparation of the transgenes of the invention. In one embodiment, the nucleotide sequence encoding the hDAF protein and that encoding the hHO-1 protein contained in the transgenes of the invention are SEQ ID NOS: 1 and 2, as shown in FIGS. 3 and 4, respectively.

Preferably, the nucleotide sequences in the transgenes of the invention are independently operably linked to a transcriptional regulatory sequence, e.g., a promoter and an enhancer, which are useful in the expression of the transgenes in the transgenic animal of the invention. In one embodiment, at least some cells, tissues, or organs of the transgenic animal of the invention, particularly heart, liver, spleen, lung, kidney, pancreas, skin, gut, blood vessels, endocrine glands, islet cells or islet, endothelial cells of blood vessels, hepatocytes, stem cells, bone marrow, and/or neurons, express the hDAF protein and/or the hHO-1 proteins. More preferably, the nucleotide sequence is linked to a tissue non-specific promoter, which allows the protein encoded by the transgene to be expressed in most cells, tissues and organs of the transgenic animals of the invention. In one embodiment of the invention, the nucleotide sequences in the transgenes according to the invention are independently linked to a chicken β-Actin promoter. By using a chicken β-Actin promoter, the products of the transgenes can be expressed in most cells, tissues and organs of the transgenic animal of the invention, e.g., heart, liver, spleen, lung, kidney, pancreas, skin, gut, blood vessels, endocrine glands, islet cells or islet, endothelial cells of blood vessels, hepatocytes, stem cells, bone marrow, and/or neurons.

The technology for the generation of a transgenic animal has been published in the prior art references (Tu C F et al., Int Surg. 1999; 84(2): 176-182, and Tu C F et al., Xenotransplantation 2003; 10(5): 503). In one embodiment, the transgenic animal of the invention is generated by collecting the embryos from animals (embryo donors), micro-injecting the hDAF and hHO-1 transgenes of the invention into the embryos, and transferring the embryos into fosters (embryo receipts) from which the transgenic animals of the invention are to be generated. Specifically, the hDAF and hHO-1 transgenes of the invention are independently constructed, purified, and diluted to an appropriate concentration, and then mixed together to obtain a transgenic DNA preparation for microinjection. The technology for construction of a transgene and its purification for generating a transgenic animal has also been well described in the prior art references, e.g., Current Protocol in Molecular Biology by Frederick et al., Massachusetts General Hospital and Harvard Medical School Press, 2002. The details are described in the following examples. In another embodiment, the present invention provides a single-gene transgenic animal.

A LPS challenge assay (see FIG. 13) demonstrates that an hHO-1 single-gene transgenic mouse generated according to the invention expressed an active and functional hHO-1 protein when the protein was present at a suitable level. Accordingly, it is expected that the hHO-1 protein expressed in the transgenic animal of the invention can act as a cytoprotective protein, which protects endothelial cells of blood vessels of the transgenic animals from apoptosis, oxidation, and inflammation. It is also expected that a transgenic animal (e.g., pig) carrying both hDAF and hHO-1 transgenes according to the invention is useful in providing cells, tissues, and organs therefrom for xenotransplantation to a human subject in need thereof, wherein the expression of the hDAF protein and/or the hHO-1 protein in the cells, tissues, and organs reduces one or more, preferably, two or more immunological rejections thereto in the human subject. In one embodiment, the expression of the hDAF protein in the cells, tissue, and organs inhibits the complement activation and thus reduces a hyperacute rejection thereto in the human subject, and the expression of the hHO-1 protein in the cells, tissue, and organs protect endothelial cells of blood vessels thereof from apoptosis, oxidation, and inflammation and thus reduces a delay vascular rejection thereto in the human subject.

III. Cells, Tissues, and Organs Isolated from the Transgenic Animal of the Invention In another aspect, the invention provides cells, tissues, and organs, isolated from the transgenic animal of the invention, which can be used as a graft for transplantation, preferably, xenotransplantation to a human subject in need thereof. Preferably, the cells, tissues, and organs isolated from the transgenic animal express the hDAF protein and/or the hHO-1 protein.

According to the invention, a graft is derived from, for instance, heart, liver, spleen, lung, kidney, pancreas, skin, gut, blood vessels, endocrine glands, islet cells or islet, endothelial cells of blood vessels, hepatocytes, stem cells, bone marrow, and/or neurons of the transgenic animal of the invention by using a conventional method. It is expected that the graft derived from the transgenic animal of the invention can be transplanted to a human subject in need thereof, wherein the expression of the hDAF protein and/or the hHO-1 protein in the graft reduces one or more, preferably, two or more immunological rejections thereto in the human subject. In one embodiment, the expression of the hDAF protein in the graft inhibits the complement activation and thus reduces a hyperacute rejection thereto in the human subject, and the expression of the hHO-1 protein in the graft protect endothelial cells of blood vessels thereof from apoptosis, oxidation, and inflammation and thus reduces a delay vascular rejection thereto in the human subject.

All methods and materials similar or equivalent to those described herein can be used in the practice of the invention. All references mentioned herein are incorporated by reference. The following examples are provided by way of illustration but not by way of limitation.

EXAMPLE

A. Material and Method

A.1 Construction of Plasmid Containing hHO-1 cDNA

Human HO-1 (hHO-1) cDNA was amplified by reverse transcriptase polymerase chain reaction (RT-PCR) from a human aortic endothelial cell total RNA pool using oligonucleotides named hHO-1cDNA-5' (SEQ ID NO: 3) and hHO-1cDNA-3' (SEQ ID NO: 4) as primers that were designed based on the published hHO-1 sequence (Yoshida T. et al., Eur. J. Biochem. 1988; 171:457).

```
hHO-1cDNA-5'
5'-TCAACGCCGAATTCCCCTCGAGCGTCCTC-3'  (SEQ ID NO: 3)

hHO-1cDNA-3'
5'-AGCCAAGAGAATTCCCTCTC-3'           (SEQ ID NO: 4)
```

The amplified hHO-1 cDNA fragment is 1026 bp in length, including one EcoRI site at each end, a 66 bp 5'-untranslated region, an hHO-1 open reading frame and a 65 bp 3'-untranslated region. The hHO-1 cDNA fragment was then inserted into the EcoRI site of pCX (Lee K H et al., J Chin. Soc. Anim. Sci. 2003; 32(2): 143-154, http://133.1.15.131/tg/sequence.cfm) to produce pCX-βActin-hHO-1 wherein a chicken β-Actin promoter is provided for driving the hHO-1 expression.

On the other hand, a PCR was performed by using oligonucleotides named HO-1Tgc-5' (SEQ ID NO: 5) and HO-1Tgc-3' (SEQ ID NO: 6) as primers and the above-mentioned pCX-βActin-hHO-1 as template to settle an EcoRI cloning site in front of the start codon of the 1026 bp hHO-1 cDNA fragment in the pCX-βActin-hHO-1 plasmid, and obtain a fragment designated as "hHO-1cDNAw/o5'UTR" that contains one EcoRI site at each end and the 3'-untranslated region as well as the hHO-1 open reading frame of the 1026 bp hHO-1 cDNA fragment, but lacks the 66-bp 5'-untranslated region of the hHO-1 cDNA fragment.

```
                                                (SEQ ID NO: 5)
HO-1 Tgc-5' 5'-CCAGCACCGAATTCATGGAGCGTCCGCAACCC-3'

(SEQ ID NO: 6)
HO-1 Tgc-3' 5'-TAAGGAAGCCAGCCAAGAGAATTCCCTCTC-3'
```

The hHO-1cDNAw/o5'UTR fragment obtained above was then inserted into the EcoRI site of pCX to produce pCX-βActin-hHO-1w/o5'UTR.

A.2 Construction of Plasmid Containing hDAF cDNA

A plasmid, pcDNA3-huCD55, that can be constructed according to Tu CF et al., Transplant. Proc. 2000; 32: 913-915, containing partial human CD55 cDNA sequences operatively linked with a cytomegalovirus (CMV) promoter, was treated with EcoRI and PvuI to remove the CMV promoter contained therein. The reminder 5.3 kb fragment was then ligated with a chicken β-Actin promoter isolated from pCX using EcoRI and PvuI to produce pcDNA3-βActin-huCD55 wherein the CD55 expression was driven by the β-Actin promoter.

On the other hand, a PCR was performed by using oligonucleotide named CD55-5' (SEQ ID NO: 7) and CD55-3' (SEQ ID NO: 8) as primers and pcDNA3-huCD55 as template to settle an EcoRI cloning site in front of the start codon of the human CD55 cDNA fragment in the pcDNA3-huCD55 plasmid, and obtain a fragment designated as "huCD55 cDNA w/o 5' UTR" that contains one EcoRI site at each end and the 3'-untranslated region and the CD55 open reading frame of the human CD55 cDNA fragment but lacks the 5'-untranslated region of the human CD55 cDNA fragment.

```
CD55-5'
5'-TAACCCGGGAATTCATGACCGTCGCGCGGC-3' (SEQ ID NO: 7)

CD55-3'
5'-ATAGGGCCCTCTAGATGAATTCTCGAG-3'    (SEQ ID NO: 8)
```

The huCD55 cDNA w/o 5' UTR fragment was then inserted into pCX to produce pCX-βActin-huCD55w/o5'UTR wherein the CD55 expression was driven by the β-Actin promoter.

A.3 Production of Transgenic Preparations for Microinjection

The pCX-βActin-hHO-1 plasmid prepared by Example A.1 was digested by SalI and HindIII to obtain a first hHO-1 transgenic DNA construct (the upper part of FIG. 1). In addition, the pcDNA3-βActin-huCD55 plasmid prepared by Example A.2 was digested by PvuI and XmaI to obtain a first hDAF transgenic DNA construct (the upper part of FIG. 2). The first hHO-1 trangenic DNA construct and the first hDAF transgenic DNA construct were separately purified by a Cesium Chloride (CsCl) gradient and a gel affinity column, and then separately diluted to a concentration of 2 to 4 ng/µl.

The pCX-βActin-hHO-1w/o5'UTR plasmid prepared by Example A.1 and the pCX-βActin-huCD55w/o5'UTR plasmid prepared by Example A.2 were digested by SalI and BamHI to obtain a second hHO-1 transgenic DNA construct (the lower part of FIG. 1) and a second hDAF transgenic DNA construct (the lower part of FIG. 2), respectively. The second hHO-1 transgenic DNA construct and the second hDAF transgenic DNA construct were separately purified by a CsCl gradient and a gel affinity column, and then separately diluted to a concentration of 2 to 4 ng/µl.

The separately purified and diluted first hHO-1 transgenic DNA construct and first hDAF transgenic DNA construct were mixed together to form a first transgenic DNA preparation. The separately purified and diluted second hHO-1 transgenic DNA construct and second hDAF transgenic DNA construct were mixed together to form a second transgenic DNA preparation. The first transgenic DNA preparation or second transgenic DNA preparation was micro-injected to the pronuclei of newly fertilized eggs or nuclear of embryos of animals (embryo donors) for the preparation of the transgenic animals according to the invention.

A.4 Animals and Treatments

A.4.1 Mice

Matured female ICR mice were obtained from National Center of Laboratory Animal and reared in a standard manner. Each female mouse was superovulated by intraperitoneal injection with 10 IU PMSG (Intervet, Holland). At 48 hour following the PMSG injection, the mouse was injected with 10 IU human chorionic gonadotropin (hCG) and mated with fertile male ICR mice as an embryo donor. Natural heated ICR mice mating with vasectomized males and checked with mating plugs were provided as foster females (i.e., embryo receipts).

Fertilized zygotes were flushed from the oviducts of the mated ICR mice, and the pronuclear embryos were micromanipulated by the Narishige manipulator with a differential interference contrast inverted microscope. The first and second transgenic DNA preparations obtained in Example A.3 were separately injected into the male pronuclear embryos, and about 25 to 30 survived embryos were immediately transferred to the fallopian tubs of the foster females. Newborn mice were born and subjected to genome analysis.

A.4.2 Pigs

Pure breed Yorkshire (Y) gilts were used in the experiments. The animals were fed with 1.0 to 1.2 kg of commercial feed twice a day and water ad libitum. Sows in lactation were fed with lactation feed and water ad libitum. The newborn transgenic piglets were weaned at the 30 to 35th day after delivery.

The gilts as embryo donors and recipients were synchronized by feeding commercial feed mixed with Regumate® (containing 0.4% altrenogest, 20 mg/day; Intervet, UK) in the morning for 15 days, superovulated by intramuscular injection of PMSG (1,500 or 2,000 IU) at the 24th hr following the last feeding of Regumate® and intramuscular injection of hCG (1,250 or 1,750 IU) at the 76th to 78th hr following the injection of PMSG, and subjected to twice artificial inseminations with pure breed Y boar's fresh-diluted semen at the 24th and 36th hr after the injection of hCG.

At the 52th to 60th hour following the hCG injection, a surgical operation was performed on the pigs as donors to flush fertilized eggs from their fallopian tubes into a dish with 20 ml Dulbecco's PBS containing 0.1% BSA. Before the operation, the donor pigs were fasted overnight and maintained calm by intramuscular injection of 5 ml sterinil and 10 ml atropine sulfate, and then anaesthetised by injection of sodium pentobarbitone at ear veins wherein the anaesthesia was maintained throughout the operation by a closed-circuit system of 4% halothene (ICI, Ltd.) in an oxygen gas mixture. The fertilized zygotes were centrifuged at 24,500×g for 8 min at room temperature (Hettich EBA 12, Germany) to expose pronuclei. The pig embryos were micromanipulated by a Leica mechanical manipulator (Leica, Germany) with a differential interference contrast inverted microscope (ZEISS Axiovert 135, Germany).

The first and second transgenic DNA preparations obtained in Example A.3 were separately injected into the male pronuclei of the pig embryos. About 25 to 30 surviving embryos were immediately transferred into the fallopian tubes of the synchronized foster pigs (i.e., embryo receipts) with the same operation procedures as for donor pigs. Piglets were then born and subject to genome analysis.

A.5. Analysis of Transgenes

The ear or tail tissues of newborn piglets and tail tissues of weaned mice were taken to extract the genomic DNAs therefrom, and the genomic DNAs were screen with the following specific primers by PCR to determine if the hHO-1 and hDAF transgenes were present in the piglets and mice:

```
hHO-1 primers
                                      (SEQ ID NO: 9)
5'-end: 5'-TCT GCT AAC CAT GTT CAT GC-3'

(SEQ ID NO: 10)
3'-end: 5'-TGG GCA ATC TTT TTG AGC ACC-3' hDAF primers
                                      (SEQ ID NO: 11)
5'-end: 5'-TCT GCT AAC CAT GTT CAT GC-3'

(SEQ ID NO: 12)
3'-end: 5'-AGA ACT CTT CAA TAT CTG ACC-3'
```

Among the primers, the hHO-1 primer at 5-end (SEQ ID NO: 9) is identical to the hDAF primer at 5'-end (SEQ ID NO: 11) since they were designed based on the same β-Actin promoter region.

The PCR reaction was conducted by heating at 94° C. for 2 minutes and performing a 35-cycle amplification, each cycle including a denaturing at 94° C. for 1 minute, an annealing at 55° C. for 1 minute, and an extension at 73° C. for 1 minute. The reaction products were analyzed by a 2% agarose gel eletrophoresis. The presence of the hHO-1 transgene was confirmed by the PCR products of 614 and 548 bp in length for the first and second hHO-1 transgenic DNA constructs, respectively (FIG. 1). The presence of the hDAF transgene was confirmed by the PCR products of 433 and 367 bp in length for the first and second hDAF transgenic DNA constructs, respectively (FIG. 2).

In addition, the genomic DNAs of positive pigs were further analyzed by Southern hybridization using the hHO-1 probes or hDAF probes, which were labeled with radioisotopes by PCR using the hHO-1 primers (SEQ ID NOS: 9 and 10) or the hDAF primers (SEQ ID NOS: 11 and 12), respectively. The genomic DNAs were treated with certain restriction enzymes and then separated in 0.8% agarose gel by electrophoresis at 25 volt for 16 hours. The DNAs in the gel were denatured by alkaline and then transferred onto a nylon membrane and separately hybridized with the hHO-1 probes and hDAF probes labeled with $^{32}$P-dCTP. The radioisotope intensity was determined by autoradiography.

A.6 Expression of Transgenes

The expression of hHO-1 and hDAF in transgenic and non-transgenic animals was analyzed by RT-PCR, western blotting and immunohistochemical (IHC) staining. The details are described below.

A.6.1 RT-PCR

Total RNAs were extracted from tissues of transgenic and non-transgenic animals using a "Phenol-Free Total RNA Isolation Kit" (RNAqueous™, Ambion, USA). The hHO-1 primers (SEQ ID NOS: 13 and 14) used for the RT-PCR were designed across at least one intron of the hHO-1 gene. The hDAF primers (SEQ ID NOS: 15 and 16) used for the RT-PCR were designed across at least one intron of the hDAF gene. The RT-PCR products for hHO-1 and hDAF transgene were 469 and 304 bp in length, respectively.

```
hHO-1 RT-PCR primer
5'-end: 5'-CCA GCA CGG AAT TCA TGG     (SEQ ID NO: 13)
AGC GTC CGC AAC CC-3'

3'-end: 5'-TGG GCA ATC TTT TTG          (SEQ ID NO: 14)
AGC ACC-3' hDAF RT-PCR primer
3'-end: 5'-TAA CCC GGG AAT TCA TGA      (SEQ ID NO: 15)
CGG TCG CGC GGC-3'

3'-end: 5'-AGA ACT CTT CAA TAT          (SEQ ID NO: 16)
CTG ACC-3'
```

A.6.2 Western Blotting

Tissues taken from transgenic or non-transgenic animals were thoroughly washed with 0.9% saline to avoid blood contamination, and then separately homogenized in a homogenization buffer (10 g sucrose, 4.0 mg pefablo SC, 0.5 mM Tris-HCl, pH 6.8, in 100 ml) by polytron (PT 3000, Switzerland). The crude homogenates were then centrifuged at 12,000×g for 5 minutes at 4° C.

The supernatant of the homogenates was removed and subjected to a SDS-PAGE and an immunoblot analysis. Briefly, the supernatant was lysed in a sample buffer (pH6.8) containing 62.5 mM Tris-HCl, 2% sodium dodecylsulfate (SDS), 5% 2-mercaptoethanol, 10% glycerol and 0.002% bromophenol blue, and then boiled for 5 minutes, cooled in an ice bath and centrifuged at 12,000×g for 3 minutes. Approximately 50 μg of the sample was subjected to a 9% SDS-PAGE wherein a bovine serum albumin (BSA) was used as a standard whose protein concentration has been determined.

When the electrophoresis was completed, the protein was transferred from the gels to a nitrocellulose membrane (Hybond-C extra, Amersham, USA) in a semi-dry transfer manner (1.2 mA/cm$^2$ for 1 hour in a transfer buffer containing 25 mM Tris-HCl, 190 mM glycine, 10% MeOH, 0.5% SDS). The membrane was incubated for 1 hour in a 5% skim milk solution (pH 7.4) containing 20 mM Tris-HCl, 500 mM NaCl and 0.05% Tween 20 (TTBS), and then rinsed with TTBS. Subsequently, the membrane was incubated with a rabbit anti-HO-1 polyclonal antibody (SPA-896, Stressgen, Canada; diluted at 1:5000 in TTBS containing 1% BSA) for 2 hours at room temperature, and washed with TTBS for three times. The membrane was reacted with a goat-anti-rabbit antibody conjugated with horseradish peroxidase (HRP) diluted 1:5000 in TTBS containing 1% BSA for 2 hours at room temperature, rinsed with TTBS for three times, and placed in a plastic bag containing a chemiluminescent working solution at a concentration of 0.125 ml/cm$^2$. The bag was rotated for 1 minute and exposed to a film.

A.6.3 IHC Staining

Ear or tail tissues were cut from transgenic and normal non-transgenic animals, rinsed with PBS, embedded in tissues freezing medium (OCT cryomatrix) (Jung, Germany) and frozen in a liquid nitrogen-ethanol solution. The tissue sections (7 μm) were mounted on slides (SuperFrost Plus, German) and then air-dried and fixed by acetone. The slides were incubated in a 0.3% $H_2O_2$ solution to block the endogenous peroxidase activity of the tissue and added with a 10% normal pig serum to block nonspecific binding.

On the other hand, the treated slides were added with rat anti-hDAF polyclonal antibody at 1:100 dilution (YD1, Serotec Inc., UK), and subsequently subjected to an avidin-biotin complex horseradish peroxidase method (VECT-STEIN ABC kit, Vector Laboratories, Inc.). Peroxidase staining was carried out using a diaminobenzidine (DAB) reagent set (Vector Laboratories, Inc). Aqueous hematoxylin was used for counterstaining.

A.7 LPS Challenge Assay

Endotoxin lipopolysaccharide (LPS) of *E. coli* (Sigma, L2880) was diluted with normal saline to a concentration of 1 mg/ml. To select a proper dose of LPS for intraperitoneal injection to the transgenic animals of the invention, a preliminary dose-response test was performed by injecting various amounts of LPS (i.e., 0, 5, 10, 20, 30, and 40 mg LPS per kg body weight (BWt) per mouse) to normal female ICR mice. Based on the results of the preliminary test, the transgenic mice prepared according to the invention were injected with 30 mg LPS per kg BWt per animal, and the survival rates were determined every day following the LPS injection for 5 to 6 days.

B. Results

As described above, after the injected embryos were transferred into the fallopian tubes of receipt females, newborn animals were borne. Their genomic DNAs were extracted and analyzed by PCR and Southern blotting to determine the presence of the hHO-1 and hDAF transgenes. The animals generated according to the invention confirmed as having the transgenes were further analyzed by RT-PCR, western blotting, and IHC staining to confirm the expression of the hHO-1 and hDAF transgenes, and by LPS challenge assay to confirm the efficacy of the transgenes.

Each line of the transgenic animals generated according to the invention is represented by specific Arabic numerals and/or English characters. Specifically, the character "A" at the end of the numbers representing the transgenic pig lines generated according to the invention as mentioned below (e.g., Y25-11A) means that the pig line was born by the females receiving embryos injected with the first transgenic DNA preparation. The character "a" at the end of the number representing the transgenic pig lines generated according to the invention as mentioned below (e.g., Y15-11a) means that the pig line was born by the female receiving embryos injected with the second transgenic DNA preparation.

B.1 Presence of Transgenes

Figure 5:
FIG. 5 illustrates the PCR results of certain lines of the pigs generated according to the invention. The upper part shows the results amplified with the hHO-1 primers used in Example A.5. The lower part shows the results amplified with the hDAF primers used in Example A.5. Lines 1 and 12 represents a 100 bp marker; Lines 2 to 7 represent the results of the pig lines Y25-01A, Y25-02A, Y25-10A, Y25-11A, Y25-12A, and Y25-13A; Line 8 represents the result of the transgenic DNA preparation for microinjection as a positive control; Line 9 represents a blank control; Line 10 represents the result of water as a negative control; and Line 11 represent the result of the transgenic mouse line 43-2 generated according to the invention as a positive control.
Figure 6:
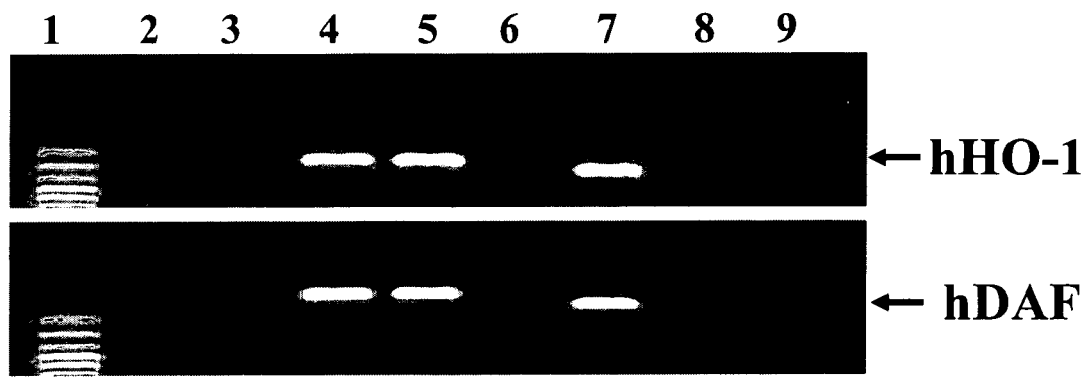
FIG. 6 illustrates the PCR results of certain lines of the pigs generated according to the invention. The upper part shows the results amplified with the hHO-1 primers used in Example A.5. The lower part shows the results amplified with the hDAF primers used in Example A.5. Line 1 represents a 100 bp water; Lines 2 to 6 represent the results of the pig littermates Y280-01a (non-transgenic), Y280-10a (non-transgenic), Y280-11a (transgenic), Y280-12a (transgenic), and Y280-13a (non-transgenic), respectively; and Line 7 to 9 represents Y25-01A (positive control), and Y105-04a (negative control) and water (blank control), respectively.
Figure 7:
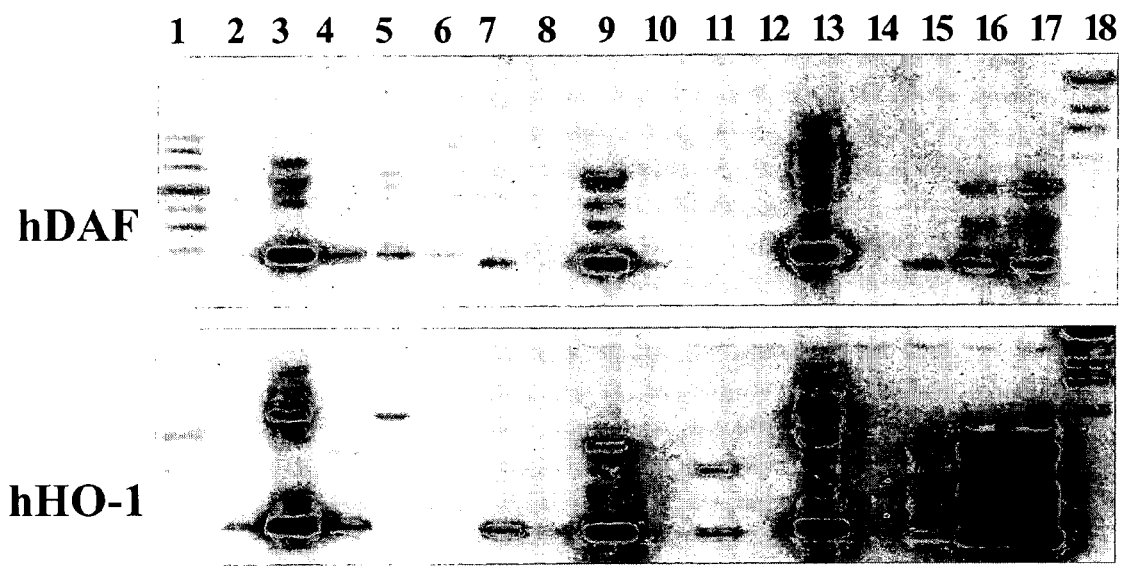
FIG. 7 illustrates the Southern blotting results of certain lines of the transgenic pigs generated according to the invention. The upper part shows the results detected with the hDAF probes used in Example A.5. The lower part shows the results detected with the hHO-1 probes used in Example A.5. Line 1 represents a 1 kb DNA ladder; Lines 2 to 14 represent the results of the transgenic pig lines Y25-01A, Y25-11A, Y25-12A, Y25-13A, Y62-11A, LY280-11a, Y15-11a, Y25-11a, Y25-12a, Y25-15a, Y44-11a, Y98-01A, and Y36-11a, respectively; Lines 15 to 17 represent one, ten and twenty copies of the DNA transgenic preparation for microinjection, respectively, as a positive control; and Line 18 represent a λHindIII marker.

FIGS. 5 and 6 illustrate the PCR results of certain lines of pig generated according to the invention. FIG. 7 illustrates the Southern blotting results of certain lines of the transgenic pig generated according to the invention.

As shown in FIG. 7, the copy numbers of the hHO-1 and hDAF transgenes vary among the transgenic pig lines generated according to the invention. Specifically, the transgenic pig line, Y44-11a, carries less than one copy of the hDAF and hHO-1 transgenes; Y25-01A, Y280-11a, Y15-11a, and Y25-15a each carry one copy of hDAF and hHO-1 transgenes; and Y25-11A, Y25-11a, and Y98-01A each carry approximately 10 to 20 copies of hDAF and hHO-1 transgenes, wherein Y98-01A is F1 transgenic progeny of Y25-11A. In addition, the transgenic pig lines of the invention, Y62-11A and Y25-12a, were confirmed as single-gene transgenic pigs, each carrying one copy of the hDAF transgene.

Table 1 illustrates the numbers of embryos, fosters (i.e., receipt females), and newborn animals borne by fosters. As illustrated in Table 1, after the embryos, injected with the first transgenic DNA preparation, were transferred into the receipt females, the fosters were pregnant and two (2) lines of hDAF/hHO-1 transgenic mice and four (4) lines of hDAF/hHO-1 transgenic pigs were generated; and after the embryos, injected with the second transgenic DNA preparation, were transferred into the receipt females, the fosters were pregnant and 13 lines of hDAF/hHO-1 transgenic mice and six (6) lines of hDAF/hHO-1 transgenic pigs were generated. However, two (2) lines of the hDAF/hHO-1 transgenic pigs, borne by the foster receiving embryos injected with the first transgenic DNA preparation, and four (4) lines of the hDAF/hHO-1 transgenic pigs, borne by the fosters receiving embryos injected with the second transgenic DNA preparation, died after birth. Finally, four (4) lines of hDAF/hHO-1 transgenic pigs (i.e., YS25-11A, Y25-13A, Y280-11a and Y15-11a) in total were healthily survived. Among the survived transgenic pig lines, Y25-11A has borne the F1 offspring, i.e., Y98-01A, which was confirmed as an hDAF/hHO-1 transgenic animal, which indicates that the hHO-1 and hDAF exogenes can be transmitted into the next generation; Y25-13A and Y280-11a were also confirmed that the exogenes can be transmitted to their offspring; and Y15-11 has been pregnant.

hHO-1 transgenic DNA construct are different from those of the first hDAF transgenic DNA construct, or the second transgenic DNA preparation, wherein the enzyme-treated ends of the first hHO-1 transgenic DNA construct are the same from those of the second hDAF transgenic DNA construct, was used. It is suggested that a gene recombination may occur between the hHO-1 and hDAF transgenes before co-integration into the animals.

B.2 Expression of Transgenes

Figure 8:
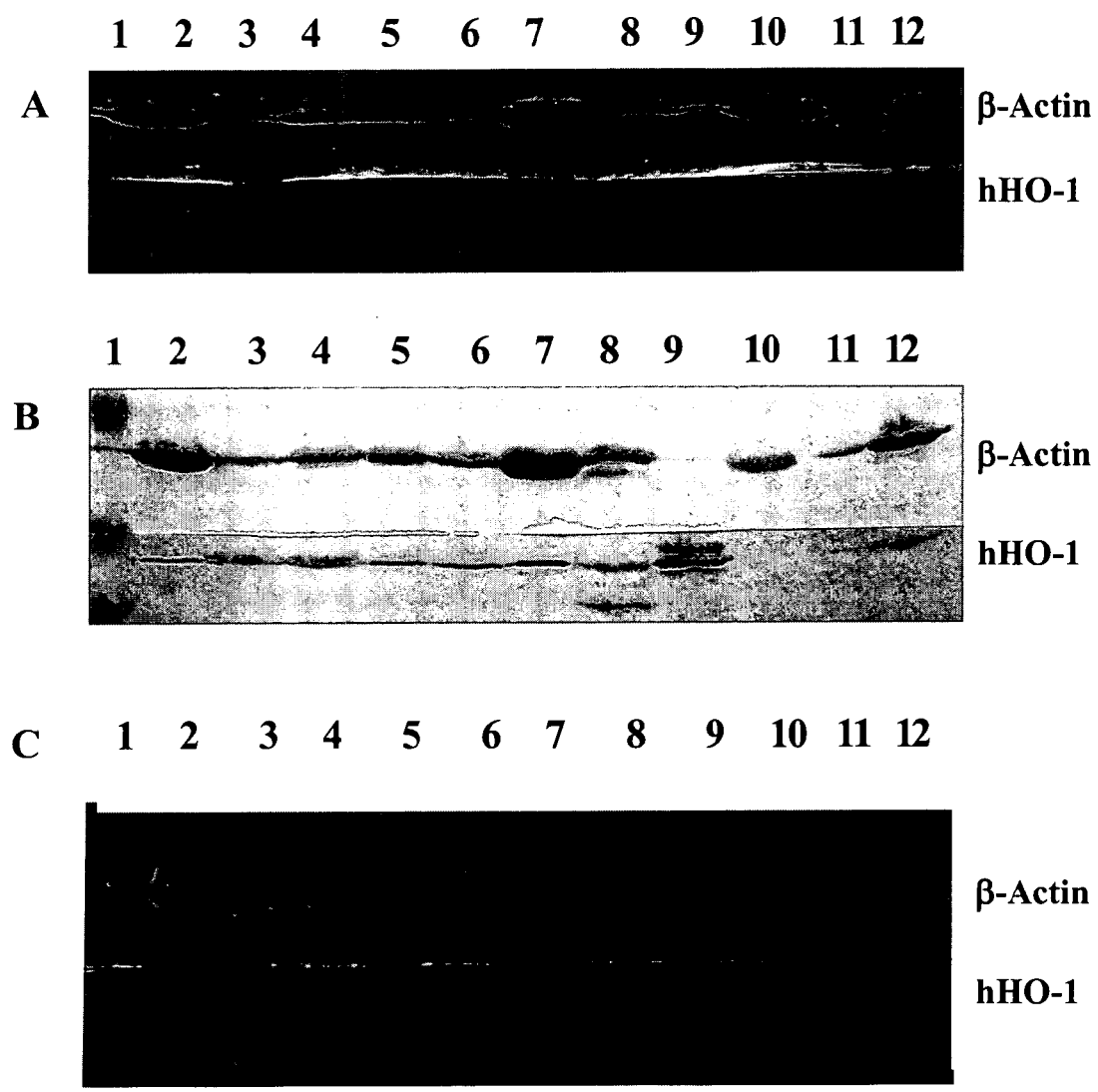
FIG. 8 illustrates the western blotting results of the offspring of the transgenic mice lines generated according to the invention. Part A represents the results of the offspring 106-2 of the transgenic mice line 27-10. Part B represents the results of the offspring 146-14 of the transgenic mice line 39-1. Part C represents the results of the offspring 156-8 of the transgenic mice line 43-2. The upper portion of each part shows the β-Actin expression results. The lower portion of each part shows the hHO-1 expression results. In Parts A and B, Line 1 represents a marker; Lines 2 to 9 represent the results of the heart, liver, spleen, lung, kidney, muscle, intestine, and pancreas of the offspring, respectively; and Lines 10 to 12 represent the results of the heart, liver, and spleen of a normal non-transgenic mouse, respectively. In Part C, each line represents the same meaning as that in Parts A and B, except that Line 8 represent the pancreas, and Line 9 represent the intestine.

Due to the use of a β-Action promoter, the RNA expression of the two transgenes was evident in each line of the transgenic mice and in various tissues of the mice (data not shown). FIG. 8 illustrates the western blotting results of the offspring (106-12, 146-14, and 156-8) of the transgenic mouse lines 27-10, 39-1, and 43-2 generated according to the invention. As shown in FIG. 8, the level of the hHO-1 protein is different in each line of the transgenic mice according to the invention. Specifically, the level of the hHO-1 protein expressed in the offspring (146-14) of the line 39-1 of the transgenic mice (Part B of FIG. 8) is higher than that in the offspring (156-8) of the line 43-2 of the transgenic mice (Part C of FIG. 8), and the latter was higher than that in the offspring (106-12) of the line 27-10 of the transgenic mice (Part A of FIG. 8).

Figure 9:
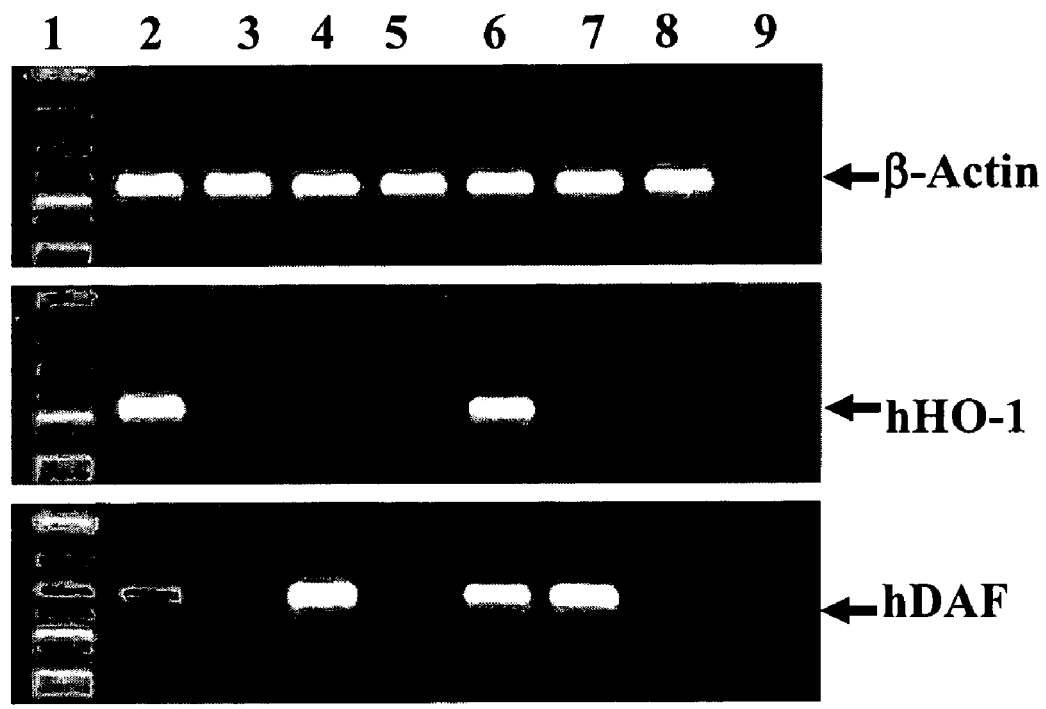
FIG. 9 illustrates the RT-PCR results of certain lines of the transgenic pigs generated according to the invention. The upper, middle and lower parts represent the results of β-Actin, hHO-1 and hDAF, respectively. Line 1 represents a 100 bp ladder; Lines 2 to 7 represent the results of the transgenic pig lines 25-11A, 25-13A, 62-11A, 280-11a, 15-11a, and 25-12a, respectively; Line 8 represents the result of a normal non-transgenic pig; and Line 9 represents the results of water as a negative control.
Figure 10:
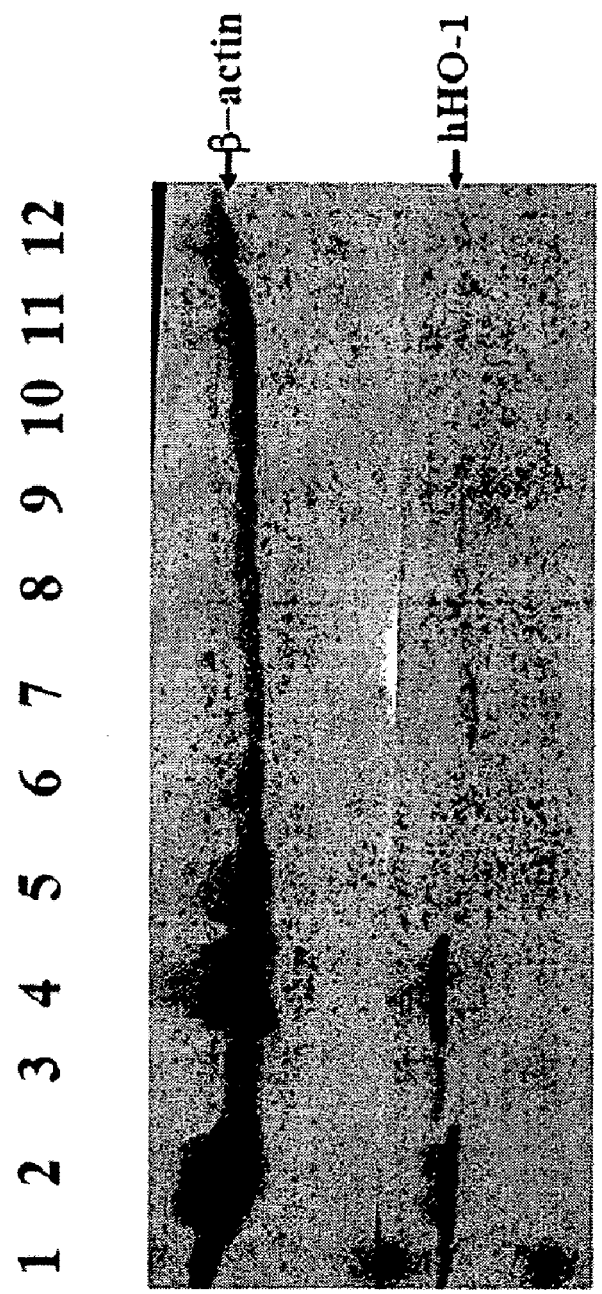
FIG. 10 illustrates the western blotting results of certain lines of the transgenic pigs generated according to the invention. The upper part shows the β-Actin expression results. The lower part shows the hHO-1 expression results. Line 1 represents a marker; Line 2 to 7 represent the results of the heart, liver, spleen, lung, kidney, and pancreas of the transgenic pig line Y25-12A, respectively; Lines 8 to 12 represent the results of the tail tissues of transgenic pig lines Y25-01A, Y25-11A, Y25-13A, Y25-02A, and Y25-10A, respectively.
Figure 11:
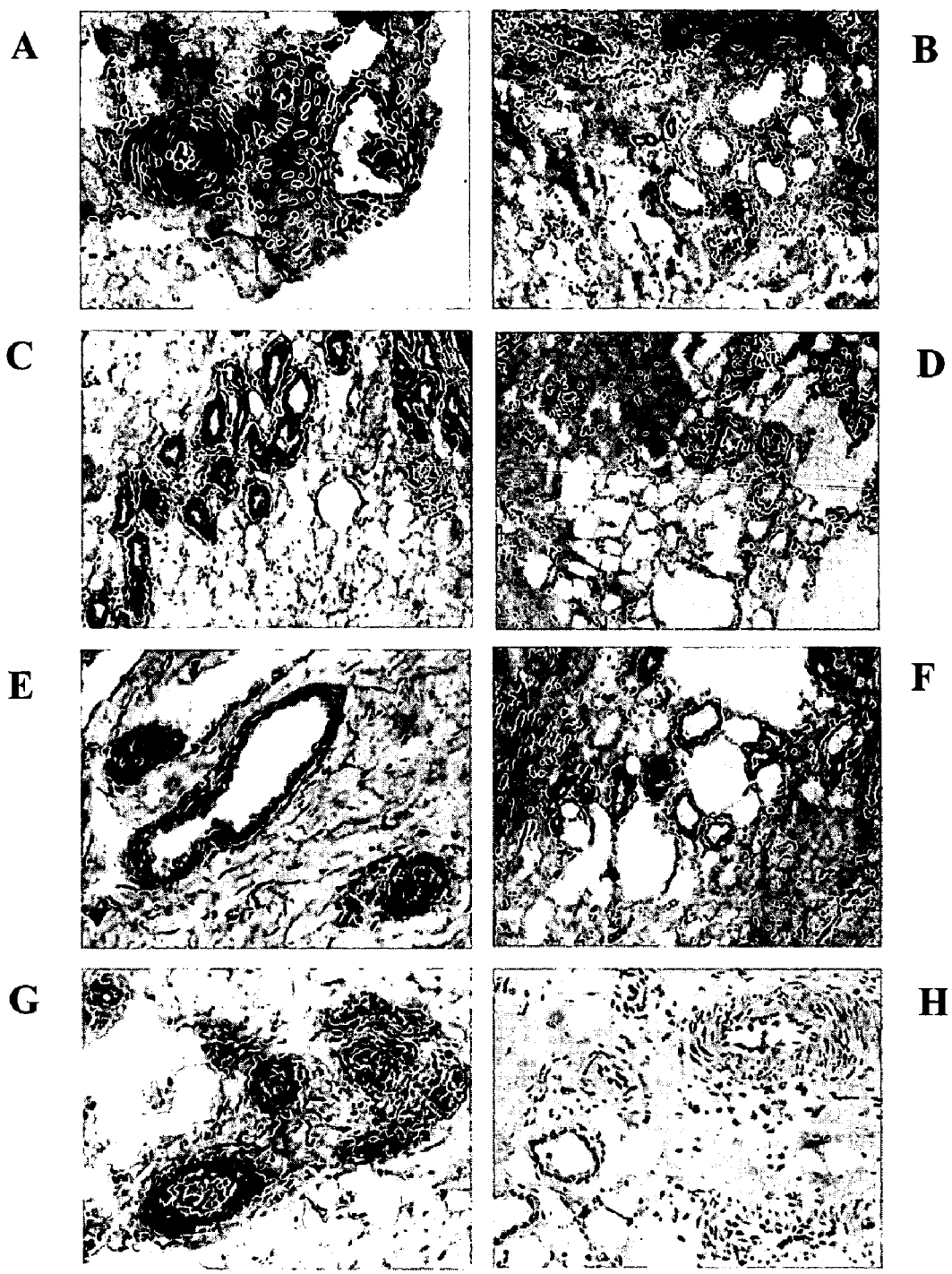
FIG. 11 illustrates the IHC staining results of certain lines of the transgenic pigs generated according to the invention.

FIGS. 9 illustrates the RT-PCR results of certain lines of the transgenic pigs generated according to the invention. FIG. 10 illustrates the results of the western blotting analysis for the hHO-1 expression in certain lines of the transgenic pigs generated according to the invention. FIG. 11 illustrates the results of the IHC staining of certain lines of the hDAF transgenic pigs generated according to the invention. The results show that, at least in the Y25-11A transgenic pig line, the RNA expression of the hHO-1 and hDAF transgenes was confirmed by the RT-PCR analysis, the protein expression of

TABLE 1

| Mice | No. of embryos | | No. of foster | | No. of newborn animals | | | |
| --- | --- | --- | --- | --- | --- | --- | --- | --- |
| | Micro-injection | Embryo transfer | Embryo transfer | Pregnant | born | hHO-1 | hHO-1/hDAF | hDAF |
| [a]1st DNA | 438 | 378 (85.4%) | 16 | 10 (62.5%) | 59 | 1 | 2 | 0 |
| [b]2nd DNA | 430 | 368 (86.3%) | 11 | 10 (90.1%) | 60 | 5 | 13 | 7 |
| Total | 868 | 742 (85.5%) | 27 | 20 (74.1%) | 119 | | 27 (22.7%) | |

| Pigs | Micro-injection | Embryo transfer | Embryo transfer | Pregnant | born | hHO-1 | hHO-1/hDAF | hDAF |
| --- | --- | --- | --- | --- | --- | --- | --- | --- |
| [a]1st DNA | 218 | 218 | 8 | 4 (50.0%) | 26 | 0 | 4[c] | 1 |
| [b]2nd DNA | 398 | 398 | 15 | 10 (66.7%) | 64 | 0 | 6[d] | 1 |
| Total | 616 | 616 | 23 | 14 (60.9%) | 90 | | 12 (13.3%) | |

[a]the first transgenic DNA preparation.
[b]the second transgenic DNA preparation.
[c]two piglets died after birth.
[d]four piglets died after birth.

As described above, the construction and purification of the hHO-1 and hDAF transgenic DNA constructs were separately performed, and the hHO-1 and hDAF transgenic DNA constructs were mixed together only when they were to be provided for microinjection. Table 1 shows a high percentage of co-integration of the separately prepared hHO-1 and hDAF transgenes into the animals according to the invention, no matter whether the first transgenic DNA preparation, wherein the enzyme-treated ends of the first the hHO-1 transgene was confirmed by the western blotting analysis, and the protein expression of the hDAF transgene was confirmed by the IHC stating; and at least in the Y15-11a transgenic pig line, the RNA expression of the hHO-1 and hDAF transgenes was proved by the RT-PCR analysis, and the protein expression of the hDAF transgene was confirmed by the IHC stating, even though the protein expression of the hHO-1 transgene in the Y15-11a line remains to be analyzed. The results of the IHC staining also show that the hDAF protein was expressed in the single-gene transgenic pig, Y25-12a, and the offspring (Y99-02) of the single-gene transgenic pig (Y62-11A) generated according to the invention.

According to the results, it appears that, in the transgenic pigs according to the invention, the protein expression of the transgenes was correlated with the RNA expression of the transgenes, but less so with the copy numbers of the transgenes. For instance, the line Y15-11a carrying only one copy of the hDAF transgene highly expressed the hDAF protein than the Y25-11A line carrying about 10 to 20 copies of the hDAF transgenes (FIGS. 7 and 11), and the line Y25-12A carrying only one copy of the hHO-1 transgene highly expressed the hHO-1 protein than the Y25-11A line (FIGS. 7 and 10).

B.3 Function of Transgenes

HO-1 can act as a cytoprotective gene in endothelial cells because of its biological activities of anti-apoptosis, anti-oxidation and anti-inflammation. The biological functions of the hHO-1 protein in the transgenic animals prepared according to the invention can be tested by in vivo challenging the transgenic animals with LPS. Example A.7 describes a LPS challenge assay for testing the biological functions of the hHO-1 protein.

In the preliminary test mentioned in Example A.7, the normal mice challenged with 30 mg LPS per kg BWt exhibited a mortality of 73.9% (17/23), and those challenged with 40 mg LPS per kg BWt exhibited a mortality of 88.9% (24/27) on the third day (i.e., 120 hours) following the LPS challenge (FIG. 12). According to the results of the preliminary test, the transgenic mice according to the invention were injected with 30 mg LPS per kg BWt, and their survival rates were measured as described above.

The results (FIG. 13) show that on the third day following the LPS challenge, the mortality of the transgenic mice line, 39-1 with a relative high hHO-1 expression level is 50.0% (7/14); the mortality of the transgenic mice line, 43-2 with a relative low hHO-1 expression level is 69.2% (9/13); and the mortality of the non-transgenic littermates is 61.9% (13/21). On the sixth day following the LPS challenge, the transgenic mouse line 39-1 with a relative high hHO-1 expression level exhibited a survival rate of 50.0%, the transgenic mice line 43-2 with a relative low hHO-1 expression level exhibited a survival rate of 7.7% (1/13), and their non-transgenic littermates exhibited a survival rate of 19.0% (4/21). The results demonstrate that the hHO-1 protein expressed in the transgenic animal according to the invention is active and functional. Accordingly, it is expected that the hHO-1 protein expressed in the transgenic animal of the invention can act as a cytoprotective protein, which protects endothelial cells of blood vessels of the transgenic animals from apoptosis, oxidation, and inflammation. It is also expected that a transgenic animal (e.g., pig) carrying both hDAF and hHO-1 transgenes according to the invention is useful in providing cells, tissues, and organs therefrom for xenotransplantation to a human subject in need thereof, wherein the expression of the hDAF protein and/or the hHO-1 protein in the cells, tissues, and organs reduces one or more, preferably, two or more immunological rejections thereto in the human subject. In one embodiment, the expression of the hDAF protein in the cells, tissue, and organs inhibits the complement activation and thus reduces a hyperacute rejection thereto in the human subject, and the expression of the hHO-1 protein in the cells, tissue, and organs protects endothelial cells of blood vessels thereof from apoptosis, oxidation, and inflammation and thus reduces a delay vascular rejection thereto in the human subject.

What is claimed is:

1. A transgenic pig having a genome including a human decay accelerating factor (hDAF) transgene having the sequence of SEQ ID NO:1 and a human heme oxygenase (hHO)-1 transgene having the sequence of SEQ ID NO:2 wherein the hDAF and hHO-1 transgenes are operably and independently linked to a chicken beta-Actin promoter, and wherein expression of the hDAF and hHO-1 transgenes results in protection of endothelial cells of blood vessels or hepatocytes of said transgenic pig from apoptosis, oxidation and inflammation.

2. The transgenic pig of claim 1, wherein cells, tissues or organs of said transgenic pig express hDAF protein and hHO-1 protein.

3. The transgenic pig of claim 2, wherein the cells, tissues or organs are heart, liver, spleen, lung, kidney, pancreas, skin, gut, blood vessels, endocrine glands, islet cells or islet, endothelial cells of blood vessels, hepatocytes, stem cells, bone marrow, or neurons.

4. Cells, tissues, or organs isolated from a transgenic pig of claim 1, which express hDAF protein and hHO-1 protein.

5. The cells, tissues, or organs of claim 4, which are heart, liver, spleen, lung, kidney, pancreas, skin, gut, blood vessels, endocrine glands, islet cells or islet, endothelial cells of blood vessels, hepatocytes, stem cells, bone marrow, or neurons.

* * * * *

SEQUENCE LISTING

```
<160> NUMBER OF SEQ ID NOS: 16

<210> SEQ ID NO 1
<211> LENGTH: 1307
<212> TYPE: DNA
<213> ORGANISM: Human

<400> SEQUENCE: 1
taacccggga attcatgacc gtcgcgcggc cgagcgtgcc cgcggcgctg cccctcctcg      60
gggagctgcc ccggctgctg ctgctggtgc tgttgtgcct gccggccgtg tggggtgact     120
gtggccttcc cccagatgta cctaatgccc agccagcttt ggaaggccgt acaagttttc     180
ccgaggatac tgtaataacg tacaaatgtg aagaaagctt tgtgaaaatt cctggcgaga     240
aggactcagt gatctgcctt aagggcagtc aatggtcaga tattgaagag ttctgcaatc     300
gtagctgcga ggtgccaaca aggctaaatt ctgcatccct caaacagcct tatatcactc     360
agaattattt tccagtcggt actgttgtgg aatatgagtg ccgtccaggt tacagaagag     420
aaccttctct atcaccaaaa ctaacttgcc ttcagaattt aaaatggtcc acagcagtcg     480
aattttgtaa aaagaaatca tgccctaatc cgggagaaat acgaaatggt cagattgatg     540
taccaggtgg catattattt ggtgcaacca tctccttctc atgtaacaca gggtacaaat     600
tatttggctc gacttctagt ttttgtctta tttcaggcag ctctgtccag tggagtgacc     660
```

| | |
|---|---|
| cgttgccaga gtgcagagaa atttattgtc cagcaccacc acaaattgac aatggaataa | 720 |
| ttcaagggga acgtgaccat tatggatata gacagtctgt aacgtatgca tgtaataaag | 780 |
| gattcaccat gattggagag cactctattt attgtactgt gaataatgat gaaggagagt | 840 |
| ggagtggccc accacctgaa tgcagaggaa aatctctaac ttccaaggtc ccaccaacag | 900 |
| ttcagaaacc taccagtaa atgttccaa ctacagaagt ctcaccaact tctcagaaaa | 960 |
| ccaccacaaa aaccaccaca ccaaatgctc aagcaacacg gagtacacct gtttccagga | 1020 |
| caaccaagca ttttcatgaa acaaccccaa ataaaggaag tggaaccact tcaggtacta | 1080 |
| cccgtcttct atctgggcac acgtgtttca cgttgacagg tttgcttggg acgctagtaa | 1140 |
| ccatgggctt gctgacttag ccaaagaaga gttaagaaga aaatacacac aagtatacag | 1200 |
| actgttccta gtttcttaga cttatctgca tattggataa aataaatgca attgtgctct | 1260 |
| tcaaaaaaaa aaaaaaaaaa ctcgagaatt catctagagg gccctat | 1307 |

<210> SEQ ID NO 2
<211> LENGTH: 1036
<212> TYPE: DNA
<213> ORGANISM: Human

<400> SEQUENCE: 2

| | |
|---|---|
| tcaacgccga attcccctcg agcgtcctca gcgcagccgc cgcccgcgga gccagcacga | 60 |
| acgagcccag caccgaattc atggagcgtc cgcaacccga cagcatgccc caggatttgt | 120 |
| cagaggccct gaaggaggcc accaaggagg tgcacaccca ggcagagaat gctgagttca | 180 |
| tgaggaactt tcagaagggc caggtgaccc gagacggctt caagctggtg atggcctccc | 240 |
| tgtaccacat ctatgtggcc ctggaggagg agattgagcg caacaaggag agcccagtct | 300 |
| tcgcccctgt ctacttccca gaagagctgc accgcaaggc tgccctggag caggacctgg | 360 |
| ccttctggta cgggccccgc tgcaggagg tcatccccta cacaccagcc atgcagcgct | 420 |
| atgtgaagcg gctccacgag gtggggcgca cagagcccga gctgctggtg cccacgcct | 480 |
| acacccgcta cctgggtgac ctgtctgggg gccaggtgct caaaaagatt gcccagaaag | 540 |
| ccctggacct gcccagctct ggcgagggcc tggccttctt caccttcccc aacattgcca | 600 |
| gtgccaccaa gttcaagcag ctctaccgct cccgcatgaa ctccctggag atgactcccg | 660 |
| cagtcaggca gagggtgata gaagaggcca agactgcgtt cctgctcaac atccagctct | 720 |
| ttgaggagtt gcaggagctg ctgacccatg acaccaagga ccagagcccc tcacgggcac | 780 |
| cagggcttcg ccagcgggcc agcaacaaag tgcaagattc tgccccgtg gagactccca | 840 |
| gagggaagcc cccactcaac acccgctccc aggctccgct tctccgatgg gtccttacac | 900 |
| tcagcttct ggtggcgaca gttgctgtag ggctttatgc catgtgaatg caggcatgct | 960 |
| ggctcccagg gccatgaact ttgtccggtg gaaggccttc tttctagaga gggaattctc | 1020 |
| ttggctggct ccctta | 1036 |

<210> SEQ ID NO 3
<211> LENGTH: 29
<212> TYPE: DNA
<213> ORGANISM: Artificial Sequence
<220> FEATURE:
<223> OTHER INFORMATION: Primer

<400> SEQUENCE: 3

| | |
|---|---|
| tcaacgccga attcccctcg agcgtcctc | 29 |

```
<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
agccaagaga attccctctc                                                    20

<210> SEQ ID NO 5
<211> LENGTH: 32
<212> TYPE: DNA
<213> ORGANISM: Artificial Sequence
<220> FEATURE:
<223> OTHER INFORMATION: Primer

<400> SEQUENCE: 5
ccagcaccga attcatggag cgtccgcaac cc                                      32

<210> SEQ ID NO 6
<211> LENGTH: 30
<212> TYPE: DNA
<213> ORGANISM: Artificial Sequence
<220> FEATURE:
<223> OTHER INFORMATION: Primer

<400> SEQUENCE: 6
taaggaagcc agccaagaga attccctctc                                         30

<210> SEQ ID NO 7
<211> LENGTH: 30
<212> TYPE: DNA
<213> ORGANISM: Artificial Sequence
<220> FEATURE:
<223> OTHER INFORMATION: Primer

<400> SEQUENCE: 7
taacccggga attcatgacc gtcgcgcggc                                         30

<210> SEQ ID NO 8
<211> LENGTH: 27
<212> TYPE: DNA
<213> ORGANISM: Artificial Sequence
<220> FEATURE:
<223> OTHER INFORMATION: Primer

<400> SEQUENCE: 8
atagggccct ctagatgaat tctcgag                                            27

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
tctgctaacc atgttcatgc                                                    20

<210> SEQ ID NO 10
<211> LENGTH: 21
<212> TYPE: DNA
<213> ORGANISM: Artificial Sequence
<220> FEATURE:
<223> OTHER INFORMATION: Primer
```

<400> SEQUENCE: 10
tgggcaatct ttttgagcac c                                                     21

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
tctgctaacc atgttcatgc                                                       20

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
agaactcttc aatatctgac c                                                     21

<210> SEQ ID NO 13
<211> LENGTH: 32
<212> TYPE: DNA
<213> ORGANISM: Artificial Sequence
<220> FEATURE:
<223> OTHER INFORMATION: Primer

<400> SEQUENCE: 13
ccagcaccga attcatggag cgtccgcaac cc                                         32

<210> SEQ ID NO 14
<211> LENGTH: 21
<212> TYPE: DNA
<213> ORGANISM: Artificial Sequence
<220> FEATURE:
<223> OTHER INFORMATION: Primer

<400> SEQUENCE: 14
tgggcaatct ttttgagcac c                                                     21

<210> SEQ ID NO 15
<211> LENGTH: 30
<212> TYPE: DNA
<213> ORGANISM: Artificial Sequence
<220> FEATURE:
<223> OTHER INFORMATION: Primer

<400> SEQUENCE: 15
taacccggga attcatgacg gtcgcgcggc                                            30

<210> SEQ ID NO 16
<211> LENGTH: 21
<212> TYPE: DNA
<213> ORGANISM: Artificial Sequence
<220> FEATURE:
<223> OTHER INFORMATION: Primer

<400> SEQUENCE: 16
agaactcttc aatatctgac c                                                     21